(12) United States Patent
Kirwan, Jr. et al.

(10) Patent No.: US 6,406,476 B1
(45) Date of Patent: Jun. 18, 2002

(54) BIPOLAR, FLUID ASSISTED COAGULATOR/ABLATOR PROBE FOR ARTHROSCOPY

(75) Inventors: Lawrence T. Kirwan, Jr., Pembroke, MA (US); Roger C. Odell, Louisville, CO (US); Joseph W. Tippett, San Antonio, TX (US)

(73) Assignee: Kirwan Surgical Products, Inc., Marshfield, MA (US)

( * ) Notice: Subject to any disclaimer, the term of this patent is extended or adjusted under 35 U.S.C. 154(b) by 122 days.

(21) Appl. No.: 09/639,370

(22) Filed: Aug. 15, 2000

(51) Int. Cl.[7] ............................................... A61B 18/18
(52) U.S. Cl. ............................. 606/50; 606/49; 606/41
(58) Field of Search ..................... 606/37–42, 45–50; 604/21, 22, 35

(56) References Cited

U.S. PATENT DOCUMENTS

| | | |
|---|---|---|
| 4,043,342 A | 8/1977 | Morrison, Jr. |
| 5,089,002 A | 2/1992 | Kirwan, Jr. |
| 5,277,696 A * | 1/1994 | Hagen ........................ 606/41 |
| 5,895,386 A | 4/1999 | Odell et al. |
| 5,925,045 A * | 7/1999 | Reimels et al. ............ 427/2.12 |
| 5,989,249 A | 11/1999 | Kirwan, Jr. |

OTHER PUBLICATIONS

Specification for INSUL–GRIP® HS–714, Insultab.

* cited by examiner

Primary Examiner—Roy D. Gibson
(74) Attorney, Agent, or Firm—Weingarten, Schurgin, Gagnebin & Lebovici LLP

(57) ABSTRACT

A bipolar, fluid assisted coagulator/ablator probe having a coaxial bipolar electrode arrangement in which an elongated outer electrode is positioned concentrically around an elongated inner electrode. An elongated concentric electrical inner insulating layer is positioned between the outer electrode and the inner electrode. An outer insulating layer is concentrically disposed over the outer electrode such that only the annular distal end of the outer electrode is exposed for surgical activity. The inner electrode is hollow and forms a conduit for drawing fluid through the probe. The inner and outer insulating layers are a high-temperature cross-linked polyethylene. In addition, the elongated hollow electrode portion is curved near the distal end of the electrode portion, and the distal end has a beveled face that forms an acute angle with a common axis of the hollow elongated probe portion.

13 Claims, 3 Drawing Sheets

BIPOLAR, FLUID ASSISTED COAGULATOR/ABLATOR PROBE FOR ARTHROSCOPY

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

Arthroscopic surgery is used to treat various conditions such as chondromalacia, or damaged articular cartilage, in joints, such as of the knee, shoulder, elbow, wrist, hip, and ankle. Articular cartilage is the tough, hyaline tissue covering the ends or articular surfaces of bones in the joints. Chondromalacia of cartilage is usually a result of diseased or traumatic induced changes in hyaline cartilage and may cause pain, stiffness, effusion, and/or grinding in the joint. A common treatment for chondromalacia involves the mechanical ablation or removal of the damaged or diseased tissue, such as with a rotary shaver. This procedure, however, may also remove healthy cartilage. Also, the rotary shaver tends to grab and tear tissue, leaving a rough surface that may slow healing and accelerate the onset of new chondromalacia.

Electrosurgical techniques have been proposed as alternatives to the mechanical ablation of tissue in arthroscopy, as well as for the coagulation of damaged and bleeding blood vessels encountered in arthroscopic surgical procedures. See, for example, U.S. Pat. Nos. 5,895,386 and 5,989,249, incorporated by reference herein. These patents disclose bipolar electrosurgical probes in which two coaxial electrodes are separated and covered by layers of an insulating material.

A problem with such prior art probes in arthroscopic surgery has been the breakdown of the insulation layers due to the high power and temperatures encountered during the use of electrosurgical instruments. Under high power, the tissue at the tip of an electrosurgical instrument may reach a temperature as high as 700° C. to 900° C. Although the temperature within the body of the probe is substantially less than 700° C., the temperature is still sufficiently high that insulation formed from a conventional polyethylene would break down and render the electrosurgical instrument inoperative within a few seconds. Typically, electrosurgical ablators for arthroscopic surgery have used a polyvinylidene fluoride (PVDF), such as KYNAR®, for the insulating layers. However, under high power, arcing at the tip of the electrodes may cause this insulating material to burn. Thus, in an arthroscopic procedure, the usable life of prior art electrosurgical instruments is limited by the insulating material. Also, the constant replacement of an inoperative instrument from the arthroscopic surgical site with a new instrument consumes both time and money and may also increase the risk of infection.

SUMMARY OF THE INVENTION

The present invention relates to a bipolar, fluid assisted coagulator/ablator probe that is capable of withstanding the high temperature, high power environment of arthroscopic surgery with an extended lifetime. The probe comprises an insulative housing and an elongated probe having a first longitudinal axis and extending from a proximal end retained within the insulative housing to a distal end extending from the insulative housing. The elongated probe further comprises a first tubular electrode forming a fluid conduit therethrough and having a first annular distal end face. A second tubular electrode is positioned concentrically around the first tubular electrode and has a second annular distal end face.

A first dielectric insulating layer is disposed between said first and second tubular electrodes, and a second dielectric insulating layer covers the second tubular electrode. The first and second dielectric insulating layers are a high temperature polyethylene capable of withstanding the high temperature, high power environment within the surgical site for at least two minutes before beginning to break down or burn.

A first bevel face is formed at the distal end of the probe, comprising the first and second annular distal end faces of the first and second electrodes, respectively. The bevel face is oriented obliquely with respect to the longitudinal axis of the probe and forms a first angle between the first bevel face and the longitudinal axis. The distal end of the elongated probe further comprises a first curve having a first radius of curvature. This configuration of the distal end is particularly suitable for use in the small arthroscopic surgery sites. The bevel face is also capable of a curette action by scraping.

DESCRIPTION OF THE DRAWINGS

The invention will be more fully understood from the following detailed description taken in conjunction with the accompanying drawings in which.

DETAILED DESCRIPTION OF THE INVENTION

The present invention relates to a bipolar, fluid assisted coagulator/ablator probe that is particularly useful for arthroscopic surgical procedures. In arthroscopic surgery, the probe may be used to coagulate bleeding blood vessels to stem the flow of blood that may occlude the surgeon's vision during the procedure. The probe may also be used to ablate or remove diseased or damaged tissues, such as articular cartilage tissue in the treatment of chondromalacia. As an ablator, the probe heats adjacent tissues to a sufficient temperature to destroy or to vaporize the cells within tissues. The destroyed or vaporized tissue is removed from the surgical site by a flow of sterile solution under suction through the probe.

Figure 1:
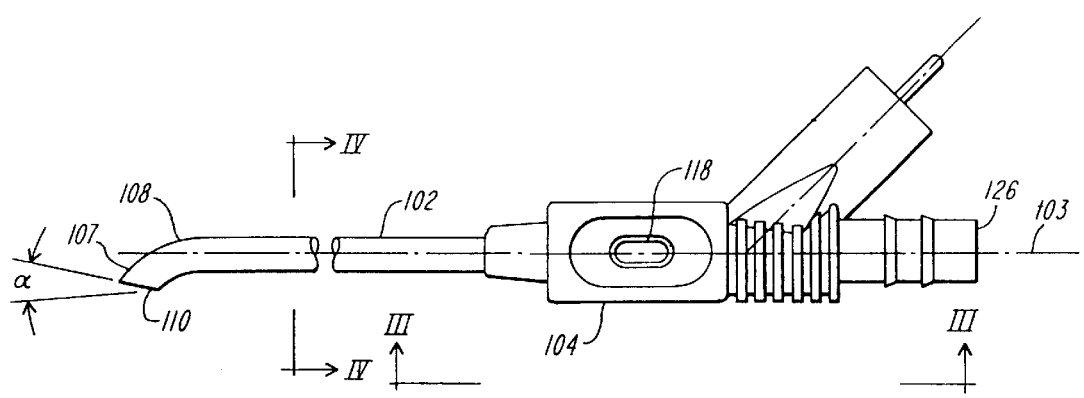
FIG. 1 is a front view of a bipolar fluid assisted coagulator/ablator probe according to this invention.
Figure 2:
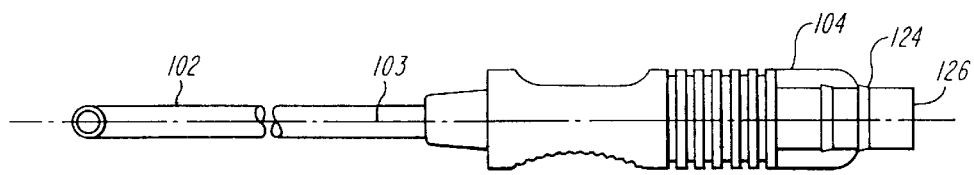
FIG. 2 is a side view of the bipolar fluid assisted coagulator/ablator probe of FIG. 1.
Figure 3:
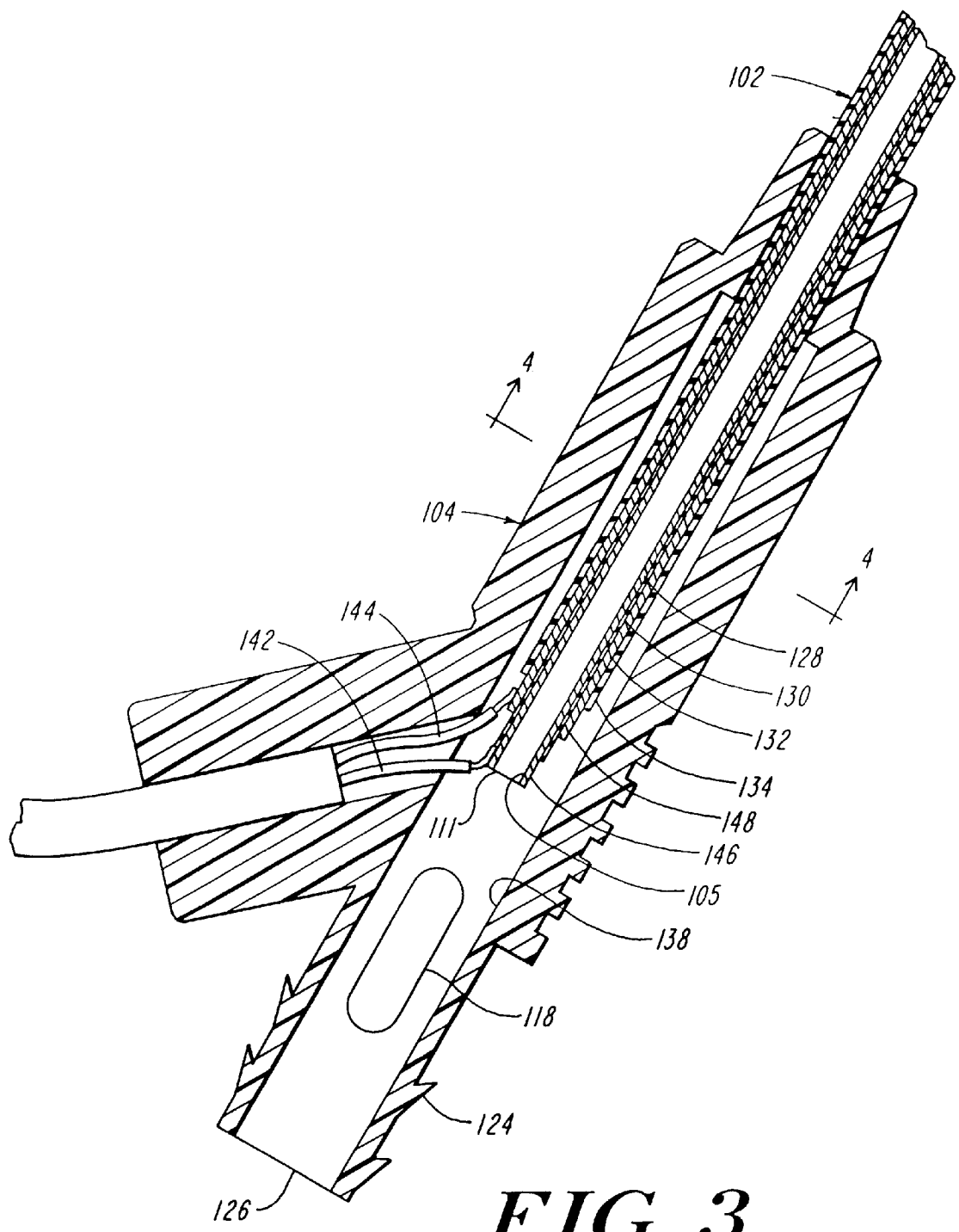
FIG. 3 is an cross-sectional view of bipolar fluid assisted coagulator/ablator probe taken along line III—III of FIG. 1.
Figure 4:
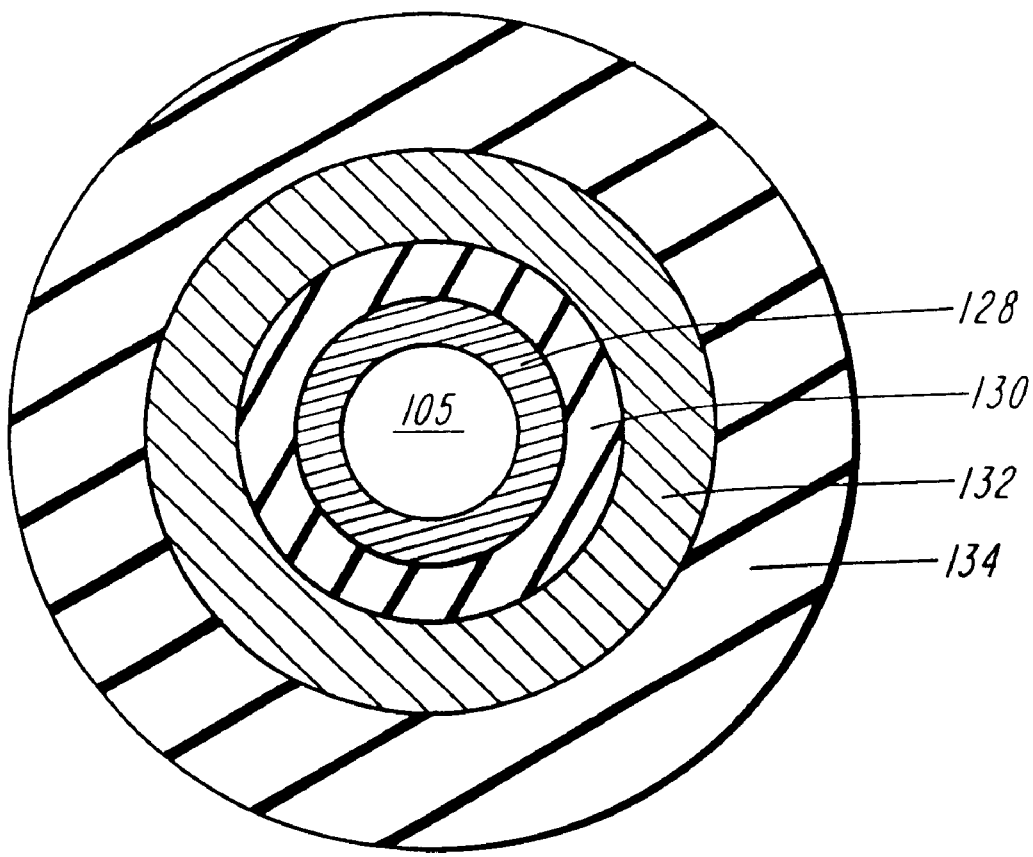
FIG. 4 is an cross sectional view of the distal end of the bipolar fluid assisted coagulator/ablator probe taken along line IV—IV of FIG. 1.

As illustrated in FIGS. 1–4, the bipolar, fluid assisted coagulator/ablator probe 100 includes a hollow electrode portion 102 extending along a longitudinal axis 103 to a curved tip or distal end 107 having an angled distal end face 110. A proximal end 111 of the electrode portion is fixed within an insulative housing 104. The electrode portion 102 includes a pair of coaxial inner and outer electrodes 128, 132. An inner dielectric insulating layer 130 separates the inner electrode 128 and the outer electrode 130. An outer dielectric insulating layer 134 covers the outer electrode 130. A fluid conduit 105 is provided within the inner electrode 128 for passage of fluid therethrough, typically to draw fluid and tissue away from the surgical site under suction, discussed further below. Preferably, the inner and outer electrodes of the hollow electrode portion 102 are made out of a malleable material, such as aluminum, that allows a surgeon to bend and shape the hollow electrode portion 102 if desired.

The inner insulating layer 130 and outer insulating layer 134 are formed from a high-temperature cross-linked polyethylene, such as an acrylated polyolefin or any other suitable material, that meets USP Class VI requirements for biocompatibility. This material is able to withstand the high temperature, high power environment at the tip of the probe during use in arthroscopic surgery for a period of at least two minutes before beginning to break down or burn.

The distal end face 180 of the inner electrode 128 and the distal end face 178 of the outer electrode 132 form an exposed annular distal end face 110 of the hollow electrode portion 102. Preferably, the distal end face of the inner insulating layer 130 is also flush with the distal end faces 178 and 180. Preferably, the outer insulating layer is recessed from the distal end face by 0.5 mm, although this is not critical. In this way, the current path from one electrode to the other through the tissue is optimized to the tissue targeted for ablation while minimizing the extent of the current path into healthy tissue.

The housing 104 provides fluid communication between the fluid conduit 105 and a suction hose (not shown) attached to a fluid pump (not shown). Toward this end, a cavity 138 is formed within the housing for fluid communication with the fluid conduit 105. The housing 104 includes a nipple end 124 having an opening 126 therein that is connectable to the suction hose from the fluid pump. The fluid pump removes fluid and tissue from the surgical site through the fluid conduit 105 and the cavity 138. The housing also includes a port 118 therein that is coverable by the surgeon's thumb to regulate the amount of suction and thus the quantity of the fluid flow through the probe, as is known in the art. It will be appreciated that any other suitable regulator valve may be used. Alternatively, the fluid pump may be operable in reverse to provide fluid to the surgical site, for example, to flush the site with a sterile solution. While fluid flow may be reversed to pump fluid into a joint during arthroscopy, the suction mode is the most significant mode for purposes of ablating chondromalacia.

The housing 104 of the bipolar, fluid assisted coagulator/ablator probe 100 also includes an extending portion that houses an end of a power cord or a power cord connector for connecting the inner and outer electrodes 128, 132 to a power source (not shown), such as an RF generator. The RF generator is selected such that the frequency and power provided by the generator are sufficient to destroy or to vaporize the tissue within the surgical site, preferably without sparking or fulguration. The inner insulating layer 130 stops short of the proximal end face of the inner electrode to expose a proximal portion 146. A first wire 142 from the power cord or power cord connector is electrically connected to the proximal portion 146 of inner electrode 128. Similarly, the outer insulating layer 134 stops short of the proximal end face of the outer electrode 132 to expose a proximal portion 148. A second wire 144 from the power cord or power cord connector is electrically connected to the proximal portion 148 of outer electrode 132.

As noted above, the tip or distal end of the electrode portion is curved and the end face is angled or beveled. The tip configuration disclosed herein has been found to be particularly suitable for use in arthroscopic surgical procedures such as the removal of chondromalacia. The bend 108 in the tip end suitably has a radius of curvature along both the inner and outer curve of between 0.3 and 0.5 inches, and preferably a radius of curvature of 0.4 inches. The dimension of the bend transverse to the longitudinal axis is suitably between 0.2 and 0.3 inches and preferably 0.27 inches. The distal end face preferably makes an angle $\alpha$ with the first longitudinal axis 103 that is between 8° and 12° and preferably is about 10°. This beveled face provides a greater exposed surface area of the outer and inner-electrodes 128 and 132 respectively. By increasing the surface area of the electrodes, a greater amount of tissue may be adjacent to the electrodes and subject to the bipolar electrosurgical action. In addition, the angle of the distal end 110 allows a curette action by scraping with the angled face.

The inner and outer insulating layers and the inner and outer electrodes are preferably circular in cross-section. With such a circular configuration, there is no rotationally preferred orientation of the hollow electrode portion 102 during surgery. Other cross-sectional configurations may be used, however, depending on the preference of the surgeon, the ease of manufacture, or the surgical area in which the device 100 is to be used. For example, the inner and outer insulating layers and the inner and outer electrodes respectively, may be oval, square, rectangular, or other shapes.

The probe may be manufactured in any suitable manner. For example, the electrodes are formed by any suitable process, such as an extrusion process. The inner insulating layer is provided as heat shrinkable tubing, such as Insul-Gripe® HS-714 manufactured by INSULTAB and available from the Woburn Company, of Woburn, Mass., over the electrode. The inner electrode and inner insulating layer are inserted in the outer electrode. The outer insulating layer is provided as heat shrinkable tubing, such as Insul-Grip® HS-714, over the outer electrode. The electrode portion is overmolded in the housing. The tip of the electrode portion is then bent to the appropriate radius, and the distal end face is ground to the appropriate angle and polished.

A probe having insulating layers formed of an acrylated polyolefin in accordance with the present invention has been manufactured and tested. Under high power, the insulating layers did not begin to degrade for 2 minutes at 700° C., which is a substantial extension in the usable lifetime over prior art coagulators.

Those of ordinary skill in the art will appreciate that variations to and modifications of the above-described bipolar fluid assisted coagulator/ablator probe apparatus and methods may be made without departing from the inventive concept disclosed herein. Accordingly, the invention should be viewed as limited solely by the scope and spirit of the appended claims.

What is claimed is:

1. A bipolar, fluid assisted coagulator/ablator probe comprising:
   an insulative housing;
   an elongated probe having a first longitudinal axis and extending from a proximal end retained within the insulative housing to a distal end extending from the insulative housing, the elongated probe further comprising:
   a first tubular electrode forming a fluid conduit therethrough and having a first annular distal end face;
   a second tubular electrode positioned concentrically around said first tubular electrode, and having a second annular distal end face;

a first dielectric insulating layer disposed between said first and second tubular electrodes;

a second dielectric insulating layer covering the second tubular electrode, wherein said first and second dielectric insulating layers are a high temperature polyethylene;

a first bevel face formed at said distal end comprising said first and second annular distal end faces, said bevel face oriented obliquely with respect to said longitudinal axis and forming a first angle between said first bevel face and said longitudinal axis;

the distal end of the elongated probe further comprising a first curve having a first radius of curvature; and first and second electrical connections electrically connected to proximal ends of first and second tubular electrodes respectively within the insulative housing and providing connection to a power source.

2. The bipolar, fluid assisted coagulator/ablator probe as in claim 1 wherein said high temperature polyethylene is a cross-linked polyethylene.

3. The bipolar, fluid assisted coagulator/ablator probe as in claim 1 wherein said first radius of curvature is between 0.2 and 0.6 inches.

4. The bipolar, fluid assisted coagulator/ablator probe as in claim 3 wherein said first radius of curvature is 0.4 inches.

5. The bipolar, fluid assisted coagulator/ablator probe as in claim 1 wherein said first angle is between 0 and 30 degrees.

6. The bipolar, fluid assisted coagulator/ablator probe as in claim 5 wherein said first angle is between 5 and 20 degrees.

7. The bipolar, fluid assisted coagulator/ablator probe as in claim 1 wherein said first angle is substantially 10 degrees.

8. The bipolar, fluid assisted coagulator/ablator probe as in claim 1 wherein said first distal region is between 0.2 and 0.3 inches.

9. The bipolar, fluid assisted coagulator/ablator probe as in claim 8 wherein said first distal region is substantially 0.27 inches.

10. The bipolar, fluid assisted coagulator/ablator probe as in claim 1 wherein said first annular distal end has a first surface area and said second annular distal end has a second surface area, and said ratio of said second surface area to said first surface area is between 1:1 and 4:1.

11. The bipolar, fluid assisted coagulator/ablator probe as in claim 1 wherein the high temperature polyethylene is an acrylated polyolefin.

12. A method of coagulating blood vessels in a surgical procedure comprising:

providing the bipolar, fluid assisted coagulator/ablator probe of claim 1; and coagulating a blood vessel with the bipolar, fluid assisted coagulator/ablator probe.

13. A method of ablating diseased or damaged tissue in an arthroscopic surgical procedure comprising:

providing the bipolar, fluid assisted coagulator/ablator probe of claim 1; and ablating the diseased or damaged tissue with the bipolar, fluid assisted coagulator/ablator probe.

* * * * *

UNITED STATES PATENT AND TRADEMARK OFFICE
CERTIFICATE OF CORRECTION

PATENT NO. : 6,406,476 B1  Page 1 of 1
DATED : June 18, 2002
INVENTOR(S) : Lawrence T. Kirwan, Jr. et al.

It is certified that error appears in the above-identified patent and that said Letters Patent is hereby corrected as shown below:

<u>Column 4,</u>
Line 33, "Gripe®" should read -- Grip® --.

Signed and Sealed this

Twenty-second Day of April, 2003

JAMES E. ROGAN
*Director of the United States Patent and Trademark Office*